United States Patent
Leconte

(10) Patent No.: US 6,579,979 B2
(45) Date of Patent: Jun. 17, 2003

(54) TREATMENT/PURIFICATION OF LACTAM MEDIA OF REACTION

(75) Inventor: Philippe Leconte, Meyzieu (FR)

(73) Assignee: Rhodia Polyamide Intermediates, Saint Fons (FR)

( * ) Notice: Subject to any disclaimer, the term of this patent is extended or adjusted under 35 U.S.C. 154(b) by 0 days.

(21) Appl. No.: 09/860,437

(22) Filed: May 21, 2001

(65) Prior Publication Data

US 2002/0030014 A1 Mar. 14, 2002

Related U.S. Application Data

(63) Continuation of application No. PCT/FR99/02823, filed on Nov. 18, 1999.

(30) Foreign Application Priority Data

Nov. 19, 1998 (FR) .............................. 98 14735

(51) Int. Cl.$^7$ ........................................... C07D 201/16
(52) U.S. Cl. ..................................................... 540/540
(58) Field of Search ......................................... 540/540

(56) References Cited

U.S. PATENT DOCUMENTS

| 2,245,129 A | 6/1941 | Greenewalt | 260/2 |
| 2,301,964 A | 11/1942 | Martin | 260/239 |
| 5,151,543 A | 9/1992 | Ziemecki | 558/459 |
| 5,496,941 A | 3/1996 | Ritz et al. | 540/540 |

FOREIGN PATENT DOCUMENTS

| DE | 8943 | 12/1951 |
| DE | 8846 | 4/1952 |
| DE | 1004616 | 3/1957 |
| DE | 1253716 | 11/1967 |
| DE | 75 083 | 8/1970 |
| EP | 0 150 295 A2 | 8/1985 |
| EP | 0 659 741 A1 | 6/1995 |
| FR | 2 029 540 | 10/1970 |
| WO | WO 96/22974 A1 | 8/1996 |
| WO | WO 98/05636 A1 | 2/1998 |

*Primary Examiner*—Bruck Kifle
(74) *Attorney, Agent, or Firm*—Burns, Doane, Swecker & Mathis, L.L.P.

(57) ABSTRACT

Lactam liquid media of reaction which comprise at least one lactam final product, notably $\epsilon$-caprolactam, are treated and purified to convert impurities contained therein into harmless species or species easily removed downstream, by hydrogenating such liquid media of reaction in the presence of a hydrogenation catalyst and during which hydrogenation the liquid media of reaction have effective lactam-purifying amounts of ammonia dissolved therein.

20 Claims, No Drawings

TREATMENT/PURIFICATION OF LACTAM MEDIA OF REACTION

CROSS-REFERENCE TO PRIORITY/PCT APPLICATIONS

This application claims priority under 35 U.S.C. §119 of FR-98/14735, filed Nov. 19, 1998, and is a continuation of PCT/FR-99/02823, filed Nov. 18, 1999 and designating the United States (published in the French language on Jun. 2, 2000 as WO 00/31031; the title and abstract were also published in English), both hereby expressly incorporated by reference.

BACKGROUND OF THE INVENTION

1. Technical Field of the Invention

The present invention relates to the treatment of lactam media of reaction and, more especially, to modifying the chemical nature of the impurities present in a reaction medium comprising a lactam final product, either in order to convert them into harmless compounds or into compounds which can be extracted or removed in downstream purification operations.

2. Description of the Prior Art

Lactams and in particular ε-caprolactam, a monomer polymerized into polycaproamide or nylon-6 (PA6), are prepared according to several synthetic processes.

The most widely used process industrially entails a Beckmann rearrangement reaction of cyclohexanone oxime with sulfuric acid or oleum, followed by the neutralization of the medium of reaction with ammonia and then by the separation and purification of the lactam thus produced.

Another process for the synthesis of the lactam entails a cyclizing hydrolysis of an aminoalkylnitrile, such as 6-aminocapronitrile in the preparation of ε-caprolactam. This reaction can be carried out in the presence or in the absence of a catalyst and either in the liquid or vapor phase. This reaction releases ammonia.

This latter process is described in numerous patents. Compare, for example, U.S. Pat. Nos. 2,357,484 and 2,301,964 and FR-2,029,540.

The process for the preparation of lactams via the vapor-phase cyclizing hydrolysis of aminonitriles is also described in EP 0,659,741 and WO 96/22974.

The conversion of aminocapronitrile to ε-caprolactam in the presence of water is exemplified in U.S. Pat. No. 2,245,129 and EP 0,150,295.

Generally, in the latter processes, aminocapronitrile is obtained by hemihydrogenation of adiponitrile by known processes described, in particular, in DE-836,938, DE-848,654 and U.S. Pat. No. 5,151,543.

As the principal application of the lactams produced is the manufacture of polymers or copolymers and more particularly of polyamides or copolyamides destined to be shaped into yarns, fibers, molded items, articles or films, the purity of the lactams must comply with and satisfy specific and strict technical specifications.

Thus, one of the primary specifications is the UV absorbance of an aqueous caprolactam solution represented by a UV number. This number is determined by measurement of the absorbance of an aqueous caprolactam solution (50% by weight) at a wavelength of 290 nm in a cell having a width of 1 cm.

In order to obtain a low UV number, it is known to this art, in particular, to subject the lactam to a hydrogenation in the presence of a catalyst.

Thus, German Patent No. 1,253,716 describes the hydrogenation of caprolactam obtained via Beckmann rearrangement in the presence of a suspended hydrogenation catalyst.

Similarly, DE-1,004,616 and East German Patent No. 75 083 describe a process for the hydrogenation of caprolactam after treatment with active charcoal and ion-exchange resins.

U.S. Pat. No. 5,496,941 describes a process for the purification of the lactam obtained by cyclizing hydrolysis of an aminonitrile. This process comprises a stage of hydrogenation of the lactam in the presence of a hydrogenation catalysts. A solvent, such as water or an alcohol, is preferably also present.

The hydrogenation stage is carried out on the isolated lactam separated from the cyclizing hydrolysis reaction mixture. This is because the subject process requires the separation from the cyclizing hydrolysis medium of the compounds which are more volatile and less volatile than caprolactam. Such separation therefore requires the removal of the ammonia produced and the distillation of the caprolactam.

The aforesaid various processes provide satisfactory results in the production of a lactam with a low UV number. However, the aforenoted purification stage adversely affects the general economics of the process. This is because the efficiency of the catalyst decreases very quickly. This short cycle time of the catalyst requires frequent replacement thereof and results in the risk of a lactam having unsatisfactory purity being obtained at the end of the catalyst cycle. This process is even more disadvantageous when the catalyst cannot be regenerated by simple and economic means.

SUMMARY OF THE INVENTION

Accordingly, a major object of the present invention is to avoid or ameliorate the above disadvantages and drawbacks to date characterizing the state of this art by providing conditions for implementing the hydrogenation stage which permit markedly increasing at least the cycle time of the hydrogenation catalysts and, thus, the overall economics of the preparation of lactams of high purity.

Briefly, the present invention features a process for the treatment/purification of a liquid medium of reaction comprising at least one lactam final product, in particular for decreasing the UV number of the lactam, which comprises hydrogenating said medium of reaction in the presence of a hydrogenation catalyst and said medium of reaction necessarily having ammonia dissolved therein.

DETAILED DESCRIPTION OF BEST MODE AND SPECIFIC/PREFERRED EMBODIMENTS OF THE INVENTION

More particularly according to the present invention, the presence of the ammonia makes it possible to significantly increase the cycle time of the hydrogenation catalyst.

To prevent or limit the condensation reaction of the lactam, the temperature at which the hydrogenation is carried out will be a temperature that promotes hydrogenation kinetics compatible with industrial application but which is as low as possible. This temperature is preferably less than 150° C., in particular when the lactam is ε-caprolactam. The temperature advantageously ranges from 50° C. to 150° C., preferably from 70° C. to 130° C.

The concentration of ammonia in the reaction medium can vary within wide proportions, but is advantageously greater than 10 g/l, and preferably ranges from 50 g/l to 200 g/l.

In one embodiment of the invention, the medium comprising the lactam includes a solvent selected, for example, from among alcohols having from 1 to 3 carbon atoms. However, the preferred solvents of the invention are water and water/alcohol mixtures. In addition, it is possible to carry out the hydrogenation of a molten lactam without a solvent other than the ammonia.

The treatment process of the invention is carried out in the presence of a hydrogenation catalyst. This catalyst can be suspended in the medium of reaction or present in the form of a fixed bed or fluidized bed deposited in a tubular reactor. The catalyst can be a bulk or supported catalyst.

The preferred catalysts of the invention are those derived from one or more metals selected from the group consisting of iron, nickel, cobalt, ruthenium, rhodium, palladium, osmium, iridium and platinum.

A catalyst support may be employed, such as, for example, active charcoal, aluminas, silicas, titanium oxides, rare earth metal oxides, such as lanthanum or cerium oxides, or zirconium or zinc oxides. A mixture of these oxides or mixed oxides may be utilized. Other catalyst supports include magnesium, aluminum or boron silicates or phosphates.

In the case of a supported catalyst, the concentration of catalytic element, expressed as weight of metal, advantageously ranges from 0.01% to 80% of the total weight of the catalyst, preferably from 0.1% to 50% by weight.

Too, the catalysts can comprise additives which improve the catalytic activity, such as, for example, zirconium, manganese, copper, chromium, titanium, molybdenum, tungsten, iron or zinc.

These doping elements typically constitute from 0% to 15% and preferably from 0.1 % to 10% by weight with respect to the catalytically active metal.

The manufacture of these supported or non-supported catalysts is described in numerous publication, such as Ullmann's *Encyclopedia of Industrial Chemistry*, Volume A5, pages 348–350, 5th edition.

The hydrogenation treatment is characteristically carried out either at atmospheric pressure or at a pressure of from 1 to 100 bar.

As noted in the prior art discussed above, this treatment with hydrogen makes it possible to decrease, in particular, the UV number of caprolactam. However, the presence of the dissolved ammonia according to the invention permits obtaining a low UV number even after a lengthy continuous operating time for the process, namely, permits treating a large amount of lactam without having to replace or regenerate the catalyst present in the reactor, or permits minimizing the consumption of catalyst per kilogram of lactam treated.

The present invention is applicable for the treatment of lactams of various origins, such as those prepared by the Beckmann rearrangement reaction, lactams obtained by depolymerization of polyamides or lactams prepared by cyclizing hydrolysis of an aminonitrile, for example.

However, this invention is more particularly applicable to the treatment of the lactam solutions obtained by hydrolysis of an aminonitrile, either in the vapor phase or in the liquid phase.

Thus, the process of the invention is more particularly applicable in the hydrogenation stages of the purification of caprolactam obtained by cyclizing hydrolysis of an aminonitrile, in the vapor phase or in the liquid phase, as described in U.S. Pat. No. 5,496,941 and WO 98/05636.

The present invention also features a process for the purification of a lactam prepared by cyclizing hydrolysis of an aminonitrile in the vapor phase and, more particularly, a process for the purification of $\epsilon$-caprolactam prepared via cyclizing hydrolysis in the vapor phase of 6-aminocapronitrile.

This process comprises:
(a) cooling the hydrolysis reaction mixture to a temperature of less than 150° C.;
(b) hydrogenating the cooled reaction mixture, containing at least a portion of the ammonia formed, in the presence of a hydrogenation catalyst;
(c) after hydrogenation, optionally separating the ammonia from the reaction mixture; and
(d) subjecting the reaction mixture to one or more downstream purification operations, to provide a lactam which satisfies desired purity specifications.

The hydrogenation treatment, carried out directly on the reaction mixture resulting from the cyclizing hydrolysis, permits using the ammonia produced in order to carry out the hydrogenation under satisfactory economic conditions, in particular with a cycle time of the catalyst which is compatible with industrial economics. If necessary, it is possible to adjust the concentration of ammonia, either by addition of ammonia or partial evaporation of the ammonia produced by the hydrolysis reaction.

Further, the subject methodology also has the effect of reducing the deterioration in the UV number which is observed during the separation of the light fractions from the reaction mixture, in particular during the distillation of the ammonia and optionally of the water or of the solvent present in the reaction mixture.

According to the present invention, the lactam recovered after the hydrogenation treatment and optionally the separation of the ammonia can be subjected to various known purification stages described in numerous patents, such as, for example U.S. Pat. No. 5,496,941, WO 98/05636, etc.

The optional treatments include oxidation, distillation in acidic or basic medium, liquid/liquid extraction, treatment over ion-exchange resins, or crystallization, for example.

All of these treatments are presented solely by way of example. It is possible for all of these to be carried out, or just certain of them, in any order.

In order to further illustrate the present invention and the advantages thereof, the following specific examples are given, it being understood that same are intended only as illustrative and in nowise limitative.

EXAMPLE 1

Comparative

An aqueous solution composed of 60 % of caprolactam prepared by a cyclizing hydrolysis of 6-aminocapronitrile, the conditions of which are set forth in French Patent Application 2,714,379, was continuously introduced into a hydrogenation reactor at a temperature of 80° C. under 25 bar of pressure charged with 5 % of Raney nickel as hydrogenation catalyst.

This caprolactam solution no longer contained ammonia, the ammonia having been distilled off on exiting the cyclizing hydrolysis stage.

The UV number of this measured solution was 24 at 290 nm.

The UV number of the solution exiting the hydrogenation stage was periodically monitored in order to determine the efficiency of the hydrogenation and thus the activity of the catalyst.

The results obtained are reported in Table I below:

TABLE I

| Operating time | 24 h | 48 h | 72 h | 120 h | 192 h |
|---|---|---|---|---|---|
| UV number | 9.7 | 22 | 22 | 23 | 23 |

These results evidence that the catalyst had lost its activity from the 2nd day of operating.

EXAMPLE 2

The procedure of Example 1 was repeated, but employing a solution of caprolactam in water to which ammonia had been added, in order to provide a solution comprising 90 g/l of ammonia and 61 % of caprolactam.

The caprolactam solution, before treatment, exhibited a UV number, measured at 290 nm, of 1.6.

The results obtained are reported in the following Table II:

TABLE II

| Operating time | 48 h | 120 h | 192 h |
|---|---|---|---|
| UV number | 0.8 | 0.8 | 0.8 |

These results clearly evidence the effect of the presence of ammonia on the preservation of the activity of the catalyst. Thus, after operating for eight days, the UV number of the resulting solution was identical to that obtained at the beginning of the operation. The hydrogenation treatment retained its efficiency.

EXAMPLE 3

The caprolactam solution treated by hydrogenation according to the conditions of Example 1 was the reaction mixture resulting from the reaction of 6-aminocapronitrile with water. This mixture was subjected to rapid cooling to a temperature of 80 ° C. at the reactor outlet, in order to prevent polycondensation of the caprolactam. The mixture comprised 90 g/l of ammonia produced by the reaction. This mixture exhibited a UV number at 290 nm of 1. 8. This mixture was subjected directly to a hydrogenation according to the conditions of Example 1.

The results obtained are reported in Table III below:

TABLE III

| Operating time | 48 h | 120 h | 192 h |
|---|---|---|---|
| UV number | 0.8 | 0.8 | 0.8 |

Furthermore, the aminocapronitrile which had not been converted to caprolactam was completely hydrogenated to hexamethylenediamine, even after the hydrogenation catalyst had been in operation for 192 hours.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the treatment and purification of a liquid medium of reaction which comprises at least one lactam final product prepared by Beckmann rearrangement, via depolymerization of at least one polyamide, or via cyclizing hydrolysis of an aminonitrile, comprising hydrogenating said liquid medium of reaction in the presence of a hydrogenation catalyst, and during which hydrogenation said liquid medium of reaction having an effective lactam-purifying amount of ammonia dissolved therein.

2. A process for the treatment and purification of a liquid medium of reaction which comprises at least one lactam final product prepared via Beckmann rearrangement, comprising hydrogenating said liquid medium of reaction in the presence of a hydrogenation catalyst, and during which hydrogenation said liquid medium of reaction having an effective lactam-purifying amount of ammonia dissolved therein.

3. A process for the treatment and purification of a liquid medium of reaction which comprises at least one lactam final product prepared via depolymerization of at least one polyamide, comprising hydrogenating said liquid medium of reaction in the presence of a hydrogenation catalyst, and during which hydrogenation said liquid medium of reaction having an effective lactam-purifying amount of ammonia dissolved therein.

4. A process for the treatment and purification of a liquid medium of reaction which comprises at least one lactam final product prepared via cyclizing hydrolysis of an aminonitrile, comprising hydrogenating said liquid medium of reaction in the presence of a hydrogenation catalyst, and during which hydrogenation said liquid medium of reaction having an effective lactam-purifying amount of ammonia dissolved therein.

5. A process for the treatment and purification of a liquid medium of reaction which comprises an $\epsilon$-caprolactam final product prepared via cyclizing hydrolysis of 6-aminocapronitrile, comprising hydrogenating said liquid medium of reaction in the presence of a hydrogenation catalyst, and during which hydrogenation said liquid medium of reaction having an effective $\epsilon$-caprolactam-purifying amount of ammonia dissolved therein.

6. The process as defined by claim 5, said liquid medium of reaction comprising an $\epsilon$-caprolactam and ammonia final product prepared via cyclizing hydrolysis of 6-aminocapronitrile in vapor phase.

7. The process as defined by claim 6, which comprises cooling the cyclizing hydrolysis reaction mixture to a temperature of less than 150° C. prior to the hydrogenation thereof, said cooled reaction mixture at least partially comprising the ammonia produced via the cyclizing hydrolysis reaction.

8. The process as defined by claim 7, comprising optionally separating ammonia from the cyclizing hydrolysis reaction mixture and optionally further purifying said $\epsilon$-caprolactam final product downstream of the hydrogenation thereof.

9. The process as defined by claim 8, comprising further purifying said $\epsilon$-caprolactam final product by distillation, oxidation, ion-exchange, crystallization and/or liquid/liquid extraction.

10. The process as defined by claim 1, said liquid medium of reaction comprising a lower alcohol, aqueous or aqueous/alcoholic solvent.

11. The process as defined by claim 1, comprising hydrogenating at a temperature of less than 150° C.

12. The process as defined by claim 1, comprising hydrogenating at a temperature ranging from 50° C. to 150° C.

13. The process as defined by claim 1, comprising hydrogenating at a temperature ranging from 70° C. to 130° C.

14. The process as defined by claim 1, said liquid medium of reaction having greater than 10 g/l of ammonia dissolved therein.

15. The process as defined by claim 1, said hydrogenation catalyst comprising iron, nickel, cobalt, ruthenium, rhodium, palladium, osmium, iridium, platinum or combination thereof.

16. The process as defined by claim 15, said hydrogenation catalyst comprising a bulk or supported catalyst.

17. The process as defined by claim 15, said hydrogenation catalyst comprising at least one additive selected from among zirconium, manganese, copper, chromium, titanium, molybdenum, tungsten, iron and zinc.

18. The process as defined by claim 16, said hydrogenation catalyst being deposited onto a support selected from among active charcoals, aluminas, silicas, titanium oxides, rare earth metal oxides, zirconium oxides, zinc oxides, magnesium and/or aluminum silicates or phosphates, and boron phosphates.

19. The process as defined by claim 18, the concentration of catalytic element in the supported catalyst ranging from 0.01% to 80% by weight.

20. The process as defined by claim 1, said liquid medium of reaction having an effective lactam UV number-reducing amount of ammonia dissolved therein.

* * * * *